US005223221A

United States Patent [19]

Copelan

[11] Patent Number: 5,223,221

[45] Date of Patent: * Jun. 29, 1993

[54] METHOD TO PREVENT TAMPERING WITH URINE SPECIMENS AND THE MEANS RELATING THERETO

[76] Inventor: Herbert W. Copelan, 8706 Via Reale, Boca Raton, Fla. 33496

[ * ] Notice: The portion of the term of this patent subsequent to Jul. 28, 2009 has been disclaimed.

[21] Appl. No.: 919,277

[22] Filed: Jul. 27, 1992

Related U.S. Application Data

[63] Continuation-in-part of Ser. No. 737,417, Jul. 29, 1991, Pat. No. 5,133,935, which is a continuation-in-part of Ser. No. 401,107, Aug. 31, 1989, Pat. No. 5,039,616.

[51] Int. Cl.[5] .................... G01N 33/94; G01N 37/00

[52] U.S. Cl. .................................... 422/61; 422/100; 422/102; 422/901; 436/56

[58] Field of Search ................ 422/61, 100, 901, 174, 422/102, 661; 436/56, 174, 180, 901; 206/459.1, 807; 4/661; 52/33, 34; 128/749, 760, 771; 358/108

[56] References Cited

U.S. PATENT DOCUMENTS 4,223,004 9/1980 Hsia et al. ............................ 436/56

4,769,215 9/1988 Ehrenkranz .................... 422/102 X 5,039,616 8/1991 Copelan ................................ 436/56

5,133,935 7/1992 Copelan ................................ 422/61

*Primary Examiner*—James C. Housel

*Assistant Examiner*—N. Bhat

*Attorney, Agent, or Firm*—Dann, Dorfman, Herrell and Skillman

[57] ABSTRACT

This invention is a method and means to prevent tampering when urine specimens are donated for testing and to do so without violating privacy. The method is to require that the hands of the donor subject be continuously engaged while the specimen container is exposed, so as not to allow the subject's hands the physical freedom necessary to introduce a false specimen into a urine container. The mans of the invention is a device that ensures that the engagement is properly followed or that shows any failure to comply. The preferred device consists of a container holder with two separate parts that lock together to make a container inaccessible to a subject. The process of hand engagement unlocks the two parts to make the container accessible. Disengagement of the hand restriction while the two units are separated relocks the mechanism and blocks reassembly.

27 Claims, 8 Drawing Sheets

METHOD TO PREVENT TAMPERING WITH URINE SPECIMENS AND THE MEANS RELATING THERETO

RELATED APPLICATIONS

The present application is a continuation in part of prior application Ser. No. 07/737,417, filed Jul. 29, 1991 and issued Jul. 28, 1992 as U.S. Pat. No. 5,133,935, which, in turn, was a continuation-in-part of U.S. application Ser. No. 07/401,107 filed Aug. 31, 1989 and issued Aug. 13, 1990 as U.S. Pat. No. 5,039,616.

BACKGROUND OF THE INVENTION AND PRIOR ART

False urine specimens are a problem for insurance and other medical examinations, but most tampering now occurs with substance-abuse testing. Substance abuse has become a major national and world problem. It affects health, safety, integrity, job performance, education, morality, the economy, crime and the general social structure. Urine testing is the most practical method of detecting active substance abuse, but it has been of limited value because of tampering and the problems in trying to prevent tampering. The incentives for a substance abuser to cheat are strong. Discovery of drug abuse can result, among other things, in criminal punishment, loss or denial of employment, and in social penalties. Thus tampering is common, and the drug abusers may be devious. Tampering is usually accomplished by a subject's introducing a false specimen into the urine container used for a test. False specimens include urine voided by a drug-free substitute subject or by the presumed subject at a time when temporarily drug-free or a fluid other than urine. A flase specimen is obtained before the test, surreptitiously taken into the private toilet compartment in the test area and introduced into the urine specimen container in place of urine presumably voided by the subject at the time of the test.

In the past the only effective way to prevent cheating has had the serious disadvantage of being offensive to most subjects. It has consisted of having an attendant watch the subject voiding into a specimen container. This procedure has been so generally unacceptable that urine testing has had only limited use. Without a watching attendant, testing is unreliable because there can be no certainty as to the donor or time of the specimen. The unsatisfactory choice, therefore, has been to risk false tests or to violate privacy. The present invention solves this problem. It ensures reliable testing without being offensive. The invention, therefore, eliminates the major objection to testing the innocent, and it does not provide the guilty with an excuse to refuse testing.

This inventor has recently developed other inventions to prevent or detect tampering with urine specimens. With one of these, the use of an ingested tag to identify a subject's urine, a subject may object to swallowing the tag or may claim, without cause, ill effects from the substance. The threat of litigation might be a deterrent to using this method. The other inventions require a complete test area designed to accomplish hand restriction. The present invention is a novel and practical hand-engaging device, which may be employed wherever desired, including a specific test area. Unlike this inventor's previous inventions, the present one need not include means to ensure the identity of the presumed subject. These should be used when necessary.

SUMMARY OF THE INVENTION

This invention consists of a method and the means to carry it out. The object of the invention is to prevent a subject from introducing a false specimen into a urine container and to prevent such tampering without visually observing the subject. The principle of the method is the use of hand engagement to restrict the subject's physical freedom to tamper. Secondarily, but essentially, the method ensures that the specimen container is inaccessible whenever the subject's hands are not engaged or else indicates that the hands were disengaged while the container was accessible.

The subject's hands are not engaged until after the subject has entered a private compartment or is otherwise allowed privacy and completed all preparations to void without further use of the hands. The subject then engages both hands by placing them on the hand holds of the device, thereby restricting the freedom of the hands to be used in other actions. Proper placement of the hands on the hand holds automatically unlocks the device and makes the container accessible for the subject to void. After the specimen is voided into the container and before the subject releases the hands from the hand holds, the container is secured so that the subject never has free access to it. The subject then disengages the hands from the hand holds and may arrange clothing and leave.

The means of the invention is a device that uses the act of hand engagement to make the urine container accessible and the act of premature disengagement to indicate a breach of procedure. The preferred embodiment comprises a two-part container holder with separating sections. When assembled and locked, the two parts keep the container inaccessible and secure from tampering. Hand engagement activates the mechanism to unlock the parts so that they can then be separated to expose the container. If the hands are disengaged while the two parts are separated, the parts cannot be properly reassembled by the subject, and the breach of procedure is evident. When the two parts are properly reassembled and the hands are then disengaged, the container is again secure.

In the preferred embodiment, one of the two parts is removable and the other is fixed. The movable part of the preferred embodiments contains the restricting hand-holds and the moving parts of the locking mechanism. In one form of the embodiment the removable part also serves as the container cover; the container is in the fixed part. In another form of the embodiment, the container is in the removable part and the fixed part serves as the cover. Simultaneous engagement of both restricting hand-holds unlocks the unit. Disengagement from a hand-hold resets the mechanism to the locked position. If this occurs prematurely, i.e. when the two parts are separated, the closed lock prevents reassembly by the subject.

Locating the hand-holds and the moving part of the simple locking mechanism in the removable part of the device makes the invention simple, reliable and easier to manufacture. The device is entirely contained in its two parts and does not need external or remote mechanisms or attendants or the transmission of external signals. It can operate by hydraulic, pneumatic, magnetic or by purely mechanical means, utilizing the subject's actions for energy. Electrical means and battery power, however, are usually preferable. Embodiments may be entirely portable and self-contained for use wherever privacy can be allowed long enough for voiding. Embodiments are adaptable for use or installation in various settings, including the test areas described in my previous patents. In all settings, the separation of the cover from the container provides full exposure of the container and allows safe and convenient use.

SUMMARY DESCRIPTION OF THE PREFERRED EMBODIMENTS

Figure 1:
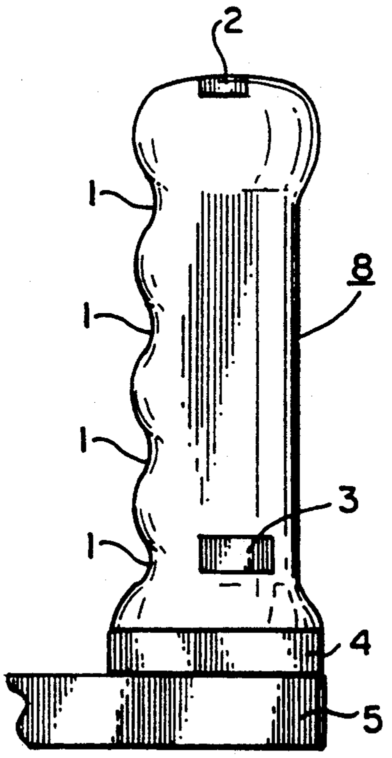
FIGS. 1 and 2 are illustrations of a hand hold for grasping by the right hand for use with the method and apparatus of the present invention.
Figure 2:
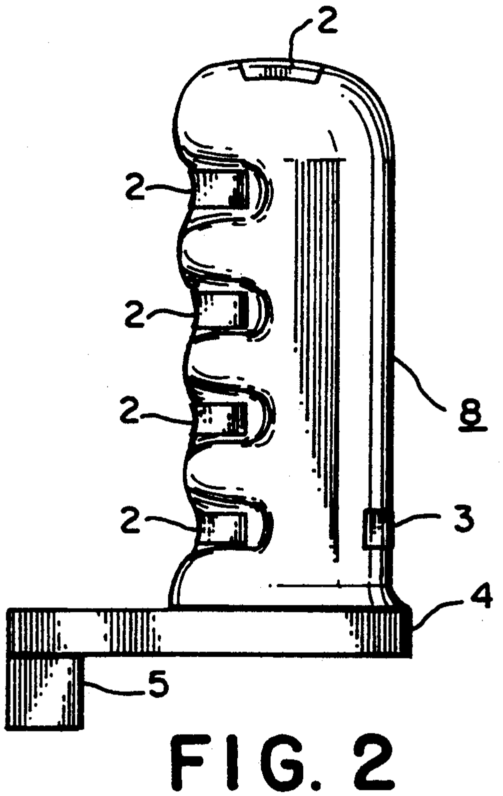

FIG. 1 is a hand-hold for the right hand viewed from the front. FIG. 2 is the hand-hold viewed from the subject's left side. The hand-hold has depressions (1) and contact actuators for the digits (2) and the base of the hand (3). A mounting fitting (4) attaches the hand-hold to the cross-bar (5) of the chassis for the embodiment shown in FIG. 7 and serves to offset the hand-hold from the mounting surface and to balance the chassis during use of this unit.

Figure 3:
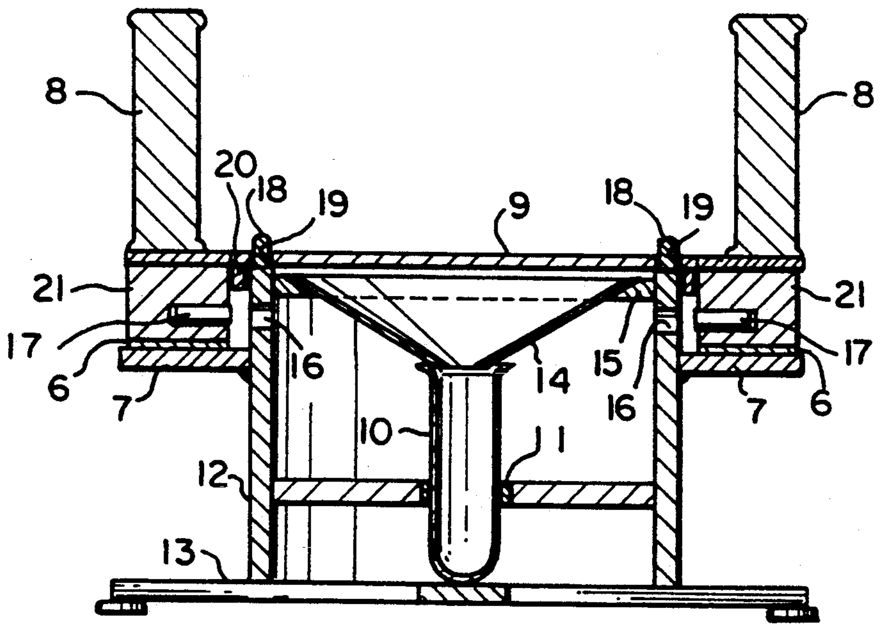
FIGS. 3–6 are diagrammatic views of a two-part container holder with supporting structure embodying the present invention.
Figure 4:
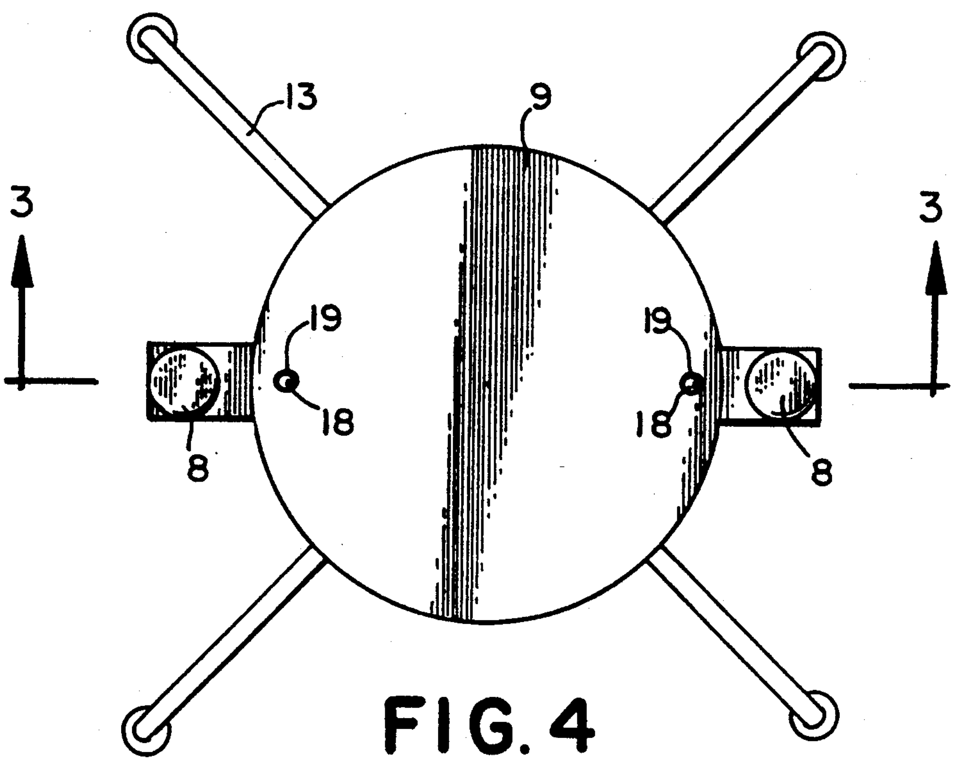
Figure 5:
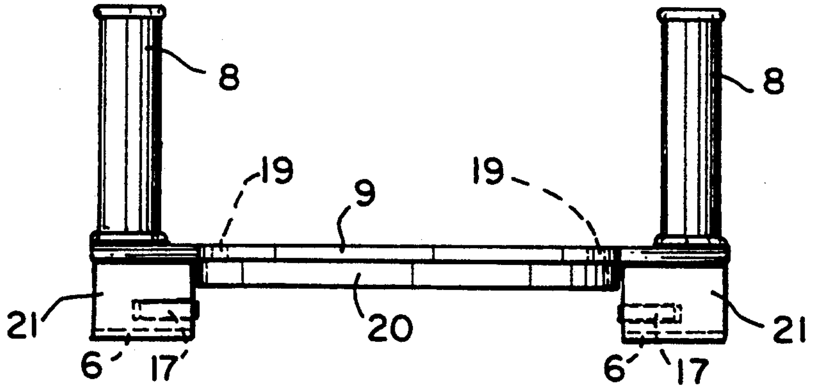
Figure 6:
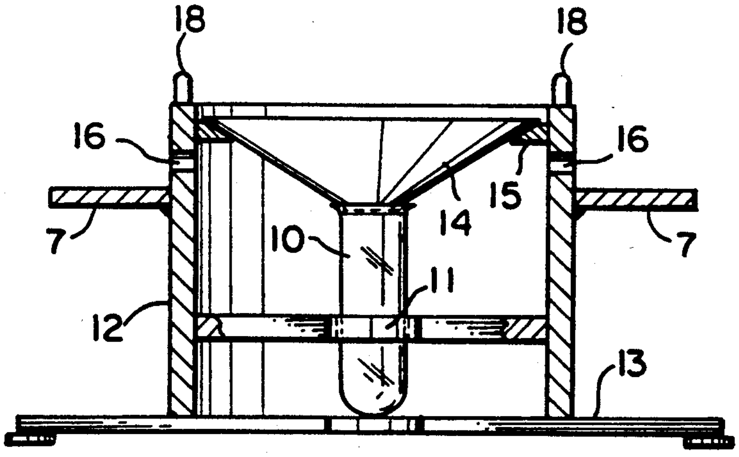

FIG. 3 is a side view and FIG. 4 is a top view of the embodiment preferred when a suitable urinal or commode is available or if the device or toilet can be suitably adapted. This embodiment can also be adapted for use without a commode or urinal. The embodiment consists of a removable, upper, container-covering unit (FIG. 5) and a lower, container-holding unit (FIG. 6). In FIG. 3 the units are fitted together, but unlocked. Hand holds (8) are fixedly attached to the container cover (9). The specimen container (10) is supported in a bracket (11) that is mounted in the cylindrical supporting structure (12) of the container-holding unit. The base (13) of the unit is relatively heavy and wide for stability. The base is the part that is most readily modified to fit variously shaped commodes or urinals. The base can also be fixed to a portable stand or camp-type toilet seat. The stand or seat can be designed to prevent or disclose its displacement by using weights, levels, sound devices, balances, or "tilt" indicators. A replaceable funnel (14) supported on a ledge (15) can be used to direct voided urine into a narrow container. Holes (16) in the cylindrical supporting structure allow the pistons (17) of the covering unit to lock the cover over the container. Guide studs (18) project from the upper edge of the supporting cylinder through holes (19) in the covering unit to insure correct replacement of the cover. A circular rim (20) on the undersurface of the cover extends down and encircles the upper, outer rim of the supporting structure when the unit is locked and further prevents access to the container. A battery-powered motor (21) retracts and extends each piston when the hand-holds are respectively engaged and disengaged. A switch (6), preferably magnetic, sets the piston motor to retract when the hand-hold contact actuators are engaged. A magnetic key (7) on the base activates the switch when the cover is fitted on the base.

Figure 7:
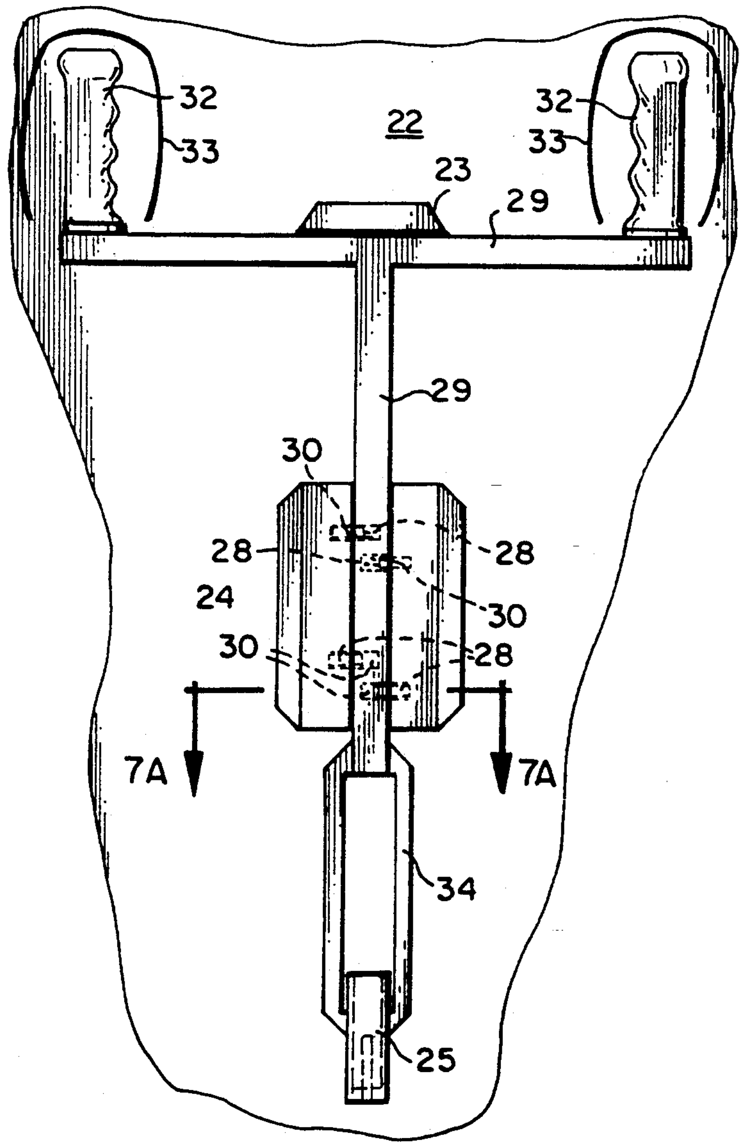
FIGS. 7–12 are views of another embodiment of a two-part holder with supporting structure embodying the present invention.
Figure 8:
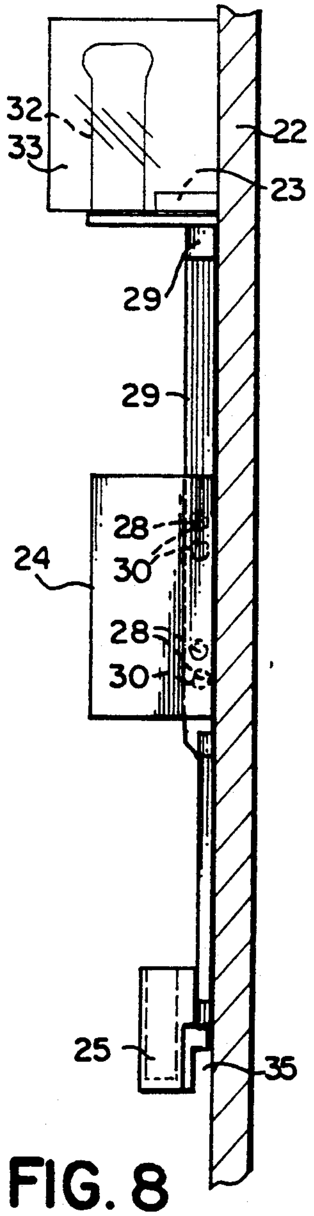
Figure 7A:
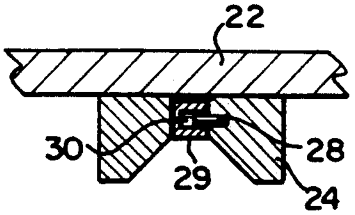
Figure 9:
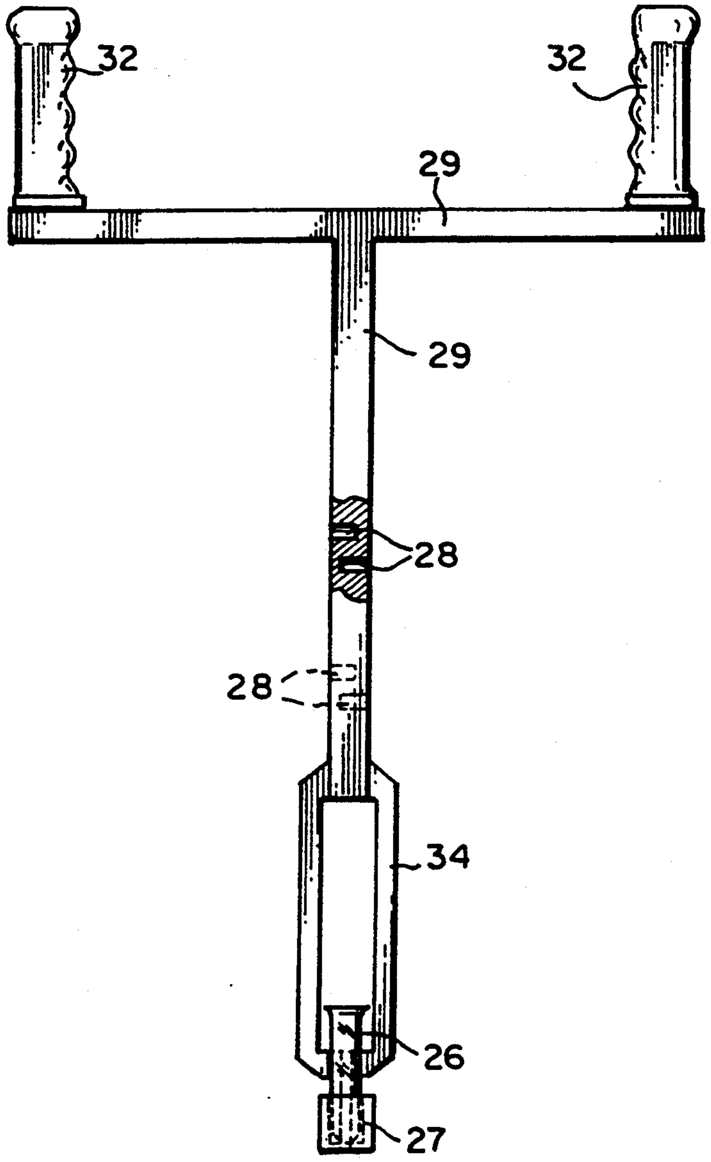
Figure 10:
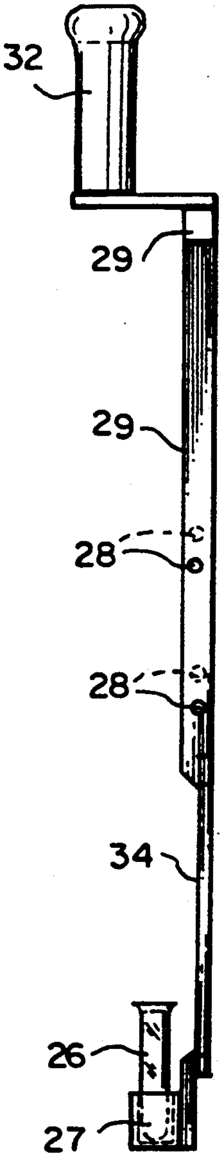
Figure 11:
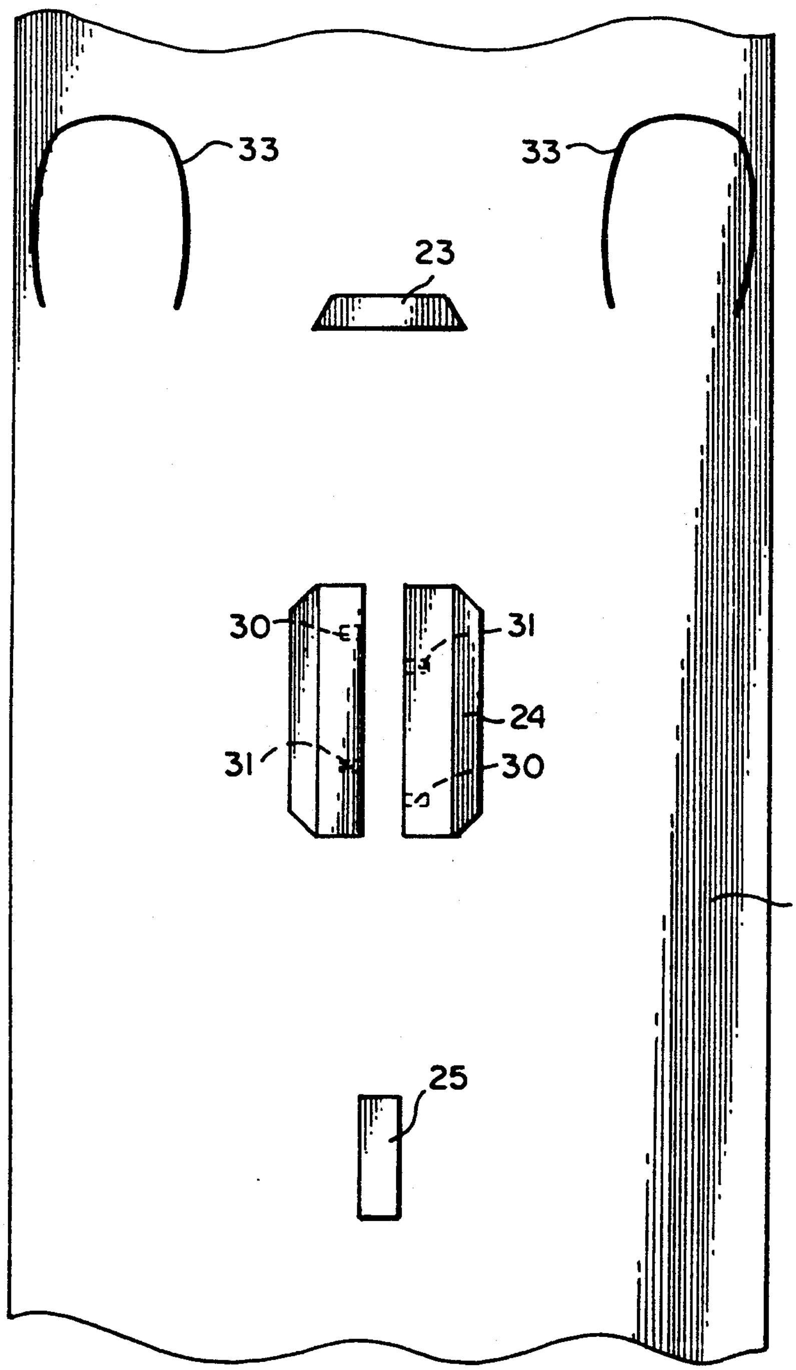
Figure 12:
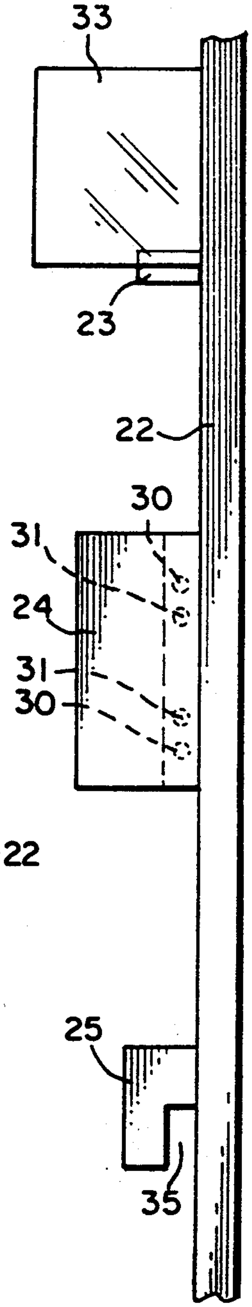

FIG. 7 is a front view of another embodiment of the invention. FIG. 8 is a side view. These figures show the removable part of the unit (FIG. 9 front and FIG. 10 side) secured on the mounting apparatus (FIG. 11 front and FIG. 12 side). The mounting surface (22) can be portable. It has brackets (23,24) which correctly position and guide placement of the "T"-shaped chassis (24). The small upper bracket (23) and the top end of the vertical, lower bracket (24) serve as stops for positioning the chassis. The container cover (25) is fixed to the mounting surface and prevents access to the container (26), which is held in the container holder (27), when the portable unit is locked in place by pistons (28). The pistons, housed in the vertical arm of the chassis (29), project out from the retracted position shown in FIG. 9 into cylinders (30) in the bracket, when the chassis is raised and secured. A needle-like "key" (31) protrudes from each cylinder base and extends into the cavity of its cylinder.

The removable unit has a hand-hold (32) for each hand with recessed contact actuators for the fingers and hand similar to FIG. 2. The hand-holds are protected by transparent sleeves (33) fixed to the mounting surface (22) and open toward the subject and inferiorly. The container holder is connected to the vertical arm of the chassis by an open rectangular frame (34) that allows movement of the frame up and down over the fixed container cover. A space (35) behind the fixed cover allows the lower, horizontal section of the frame bracket to fit up into the cover.

Figure 13:
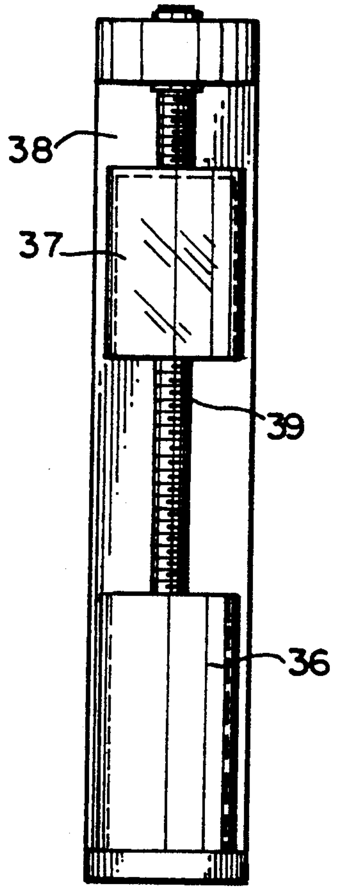
FIGS. 13 and 14 are views of another embodiment of a two-part holder for use with the support structure of FIGS. 7–12.
Figure 14:
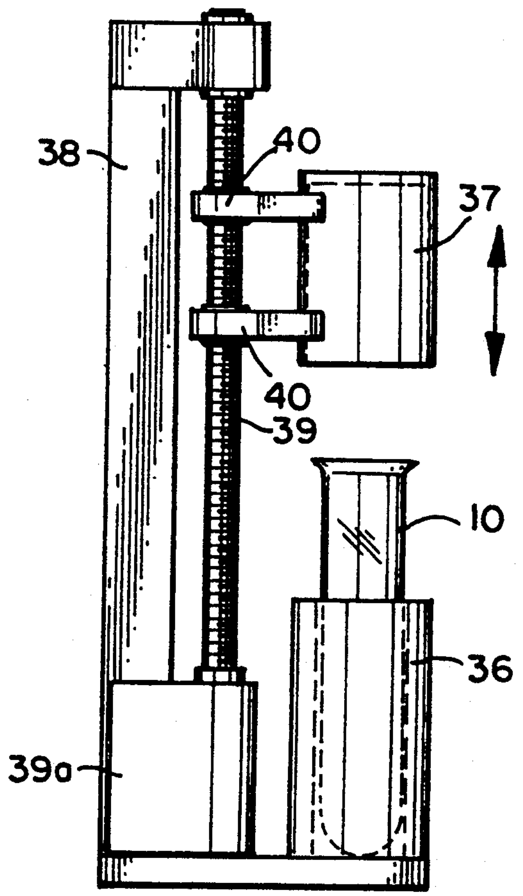

FIG. 13 (front view) and FIG. 14 (side) show the container holder (36) and covering element (37) of a self-contained, single unit that resembles the portable part of the embodiment of FIGS. 7 through 12. The cover is attached to the vertical arm (38) of the chassis rather than fixed to a mounting wall. The cover is raised and lowered by a threaded driving rod (39) and connecting, geared links (40) on the cover.

Figure 16:
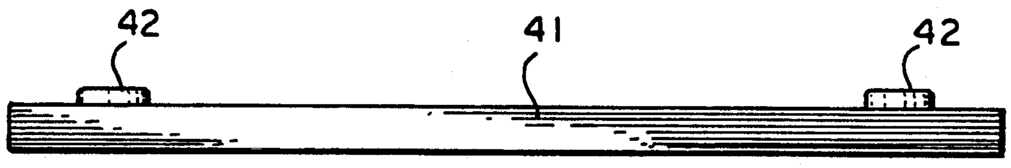
FIGS. 15 and 16 illustrate a treadle plate for engaging the feet of a subject in accordance with the present invention.
Figure 15:
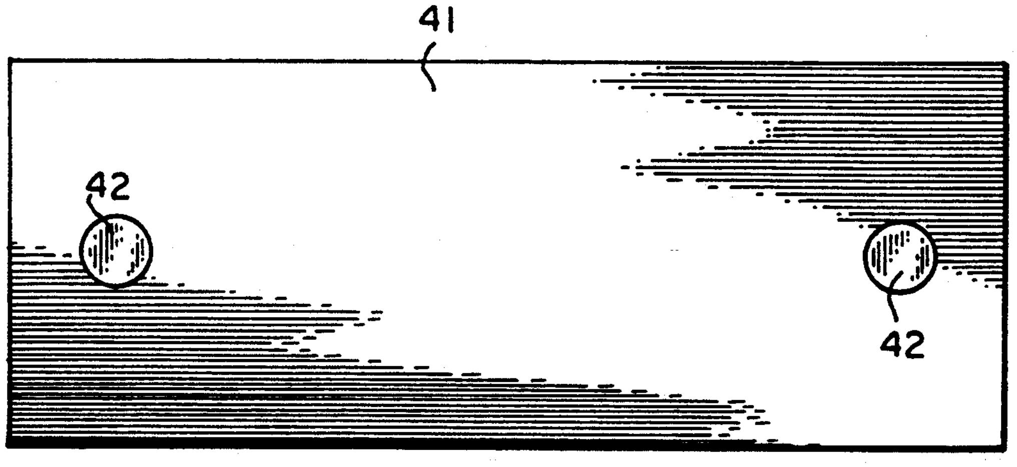

FIG. 15 (top view) and FIG. 16 (side) show a simple attachment that may be used with the embodiments shown in to restrict the location of the feet and thereby the legs. It consists of a base plate (41) with a switch (42) at each end. The switches 42 are contact actuators which may control access to the container by engagement or disengagement of each foot with the associated switch.

DETAILED DESCRIPTION OF THE INVENTION

Grasping by the subject's hands on the hand holds of this invention ensures that the subject's hands are not close to the urine container when it is available for filling. The hand holds preferably are located far enough apart, so that the arms also cannot be used to extract, support or manipulate a false specimen and introduce it into the container. Hand engagement is accomplished preferably by placing the fingers on contact actuators. This element of the invention can utilize technology widely applied in finger switches and touch contacts used in household appliances, electronic units and their remote controls, garage-door openers, automatic teller machines, computer screens, keyboards and elevator and door controls among others. Mechanical switches, levers and buttons are less desirable alternatives. Elaborate embodiments of this invention could utilize sensors for heat, light and motion and infra-red, radio and ultrasonic signals among others, but simple electronic touch contacts are preferred. In the following description, contact actuators are identified as contacts.

Both hands grasping the hand holds engages hand so that the hand must remain within its designated grasping position, sufficiently distant from the urine container. Embodiments can use a silhouette outline to guide placement of the hands. In the preferred embodiments the silhouette can be inscribed around the contoured hand-hold shown in FIGS. 1 and 2. The restricting hand-holds preferably have separate contacts for each of the digits and the base of the hand. (For a subject with a deformed or amputated finger a contact could be bypassed). The finger contacts are placed near the positions for the finger tips and are separated from each other so that they must be engaged by discrete elements, such as the several digits, rather than by a signle mass. The finger positions and contacts preferably are depressed from the surface of the supporting structure. (Additional refinements can include intermediate contacts to disable the system or alert an attendant if a subject attempts to engage the contacts by an object that does not have the configuration of the respective hand. Heat or pulse sensors and other more sophisticated refinements for the contacts can also be used. External signals that indicate the engagement of contacts and removal of the unit also might have some value. All of these refinements add complexity, however, and are not preferred.)

FIGS. 3 through 6 represent the embodiment preferred when there is a suitable commode or urinal or when there is opportunity to modify details of the embodiment or an existing toilet. When fixed to a portable stand or seat, the embodiment can be used without a commode or urinal. The basic operation of the invention is not affected by such changes. When fitting is possible, this embodiment is preferred because of its simplicity, reliability, safety, convenience and sanitary advantage.

Hand engagement is accomplished preferably with hand-holds similar to those described above. The hand holds may be mounted horizontally, particularly for commode units. Approximately simultaneous engagement of all the contacts on both hand-holds is required to retract the pistons that lock the cover over the container. Other locking systems may be used instead of pistons. Disengagement from any contact actuator returns the piston to the locking, projecting position. A programmed delay or, preferably, a specific key (magnetic preferably, but mechanical or wireless means are also feasible) is needed to retract the piston. The key may be an integral part of the base so as to fit precisely against a switch contact for the piston-retracting motor. The key sets the switch for the motor to retract the piston when the hands engage the contacts. If the cover is not in place the key does not activate the switch and the pistons are not retracted. (A portable key can be available for an attendant.) Thus, if a subject disengages prematurely, the cover cannot fit into its locking position, and the premature disengagement and possible tampering is evident. All circuits and linkages are preferably continuous and contained within the cover unit. Wireless and other types of signal transmission are not needed. This simplifies fully mechanical operation, but electronic sensing and battery-powered electric motors are preferred.

The possibility for successfully introducing a false specimen into the container is remote. A subject might conceivably enter a private toilet compartment with a concealed, false specimen; place it in the mouth; then engage both hands to unlock the device; raise the cover and bend over the container to eject the specimen. Such attempts can be frustrated by attaching the cover to the container-holding unit with short tethers at each end. The tethers would allow space for voiding but prevent access for the head. The cover in such a modification should be largely transparent so that a subject can see the container in order to void.

Additionally, to prevent such tampering, when the device is installed in a urinal, it is preferable to limit the space in front of the urinal. The cross section of this area should not allow enough knee and hip flexion to bring the head close to the container when both hands are engaged on a tethered cover. Also, to limit knee flexion, the urinal should not project far from its supporting wall. When the device is installed in a commode, it is preferably to limit the space on each side of the commode. A subject cannot then kneel beside the commode to bring the head close to the container when the hands are restricted on a tethered cover. (The spatial configuration of the hand-hold contacts does not allow a subject to engage them except from the commode side). Neither of these space limitations affects convenience.

A foot attachment as shown in FIGS. 15 and 16 is unnecessary for this embodiment, because the container is in the part of the unit that is fixed in a urinal or commode. Raising the removable part that covers the container would dislodge a false specimen container held between the legs over a commode. When the container is fixed in a urinal, it is too high to be filled from the level of the legs. Although various guards can be used for the hand-holds, guards are not preferred for this embodiment. It is difficult to circumvent the requirement for simultaneous engagement of all the contacts; and guards, although feasible, would make the device less convenient for installation and use.

The embodiment of the present invention shown in FIGS. 7–12 is useful when the embodiment of FIGS. 3 through 6 cannot be fitted to an available toilet or stand particularly for male subjects. It consists of a mounting unit that includes the cover for the container and a removable unit, preferably a "T"-shaped chassis fitted with two hand-engaging devices, a container-holder and a locking mechanism to secure the container and its holder when the chassis is locked in the mounting unit. To make the container accessible, the restricting hand-holds are grasped to unlock the chassis from its verticle mounting bracket. The chassis, held by the subject, is lowered until the cross-bar rests against the top of the vertical mounting bracket. At this position the container has cleared the container cover. The open, rectangular bracket, which connects the container holder to the lower end of the vertical bar, is free to pass over the container holder, and the unit can be removed. By positioning the chassis, the container in its holder is placed to collect the subject's urine as it is voided. The procedure is reversed to replace the unit. When the unit is returned to its proper position with the cross-bar raised to the upper stop, the pistons are aligned with the cylinders and lock when the hands are disengaged.

The chassis is constructed of a light-weight, rigid material, preferably a metal alloy. It is non-corrosive in its lower portion, which includes the container-holder and its connecting frame. The upper section of the chassis is represented by the cross-bar of the "T" and is fitted with a hand-restricting hold at each end of the cross-bar. The hand-hold contacts preferably are connected by circuit to small motors that work the locking mechanisms. All contacts for both hands must be activated approximately simultaneously. An excessive interval activates a delayed circuit-breaker in the preferred embodiment, and no unlocking signal is sent.

When the chassis is in its mounted position, the hand-holds preferably lie within transparent, plastic, cylindrical guards fixed to the mounting surface (alternatively, they can be fixed to the cross-bar of the chassis) to prevent tampering with the contacts. These guards are open at the front and below. Various types of guards can be used to prevent tampering with the hand-holds while permitting easy access for hand engagement and to allow the chassis to be lowered from its locked position. The locking mechanism of the preferred embodiment consists of at least one piston housed in the vertical bar of the chassis and the cylinder in the vertical mounting bracket to lock the unit. The bracket holds and aligns the vertical section of the chassis and allows the chassis to be moved up and down. The open side of the vertical bracket preferably is flared outward to allow easy replacement of the chassis. The small bracket mounted above the cross-bar of the chassis and the top of the lower vertical bracket serve as stops to limit the excursion of the chassis while allowing sufficient vertical movement to free the container and its holder.

The container holder is slightly wider than the external diameter of the urine specimen container and its depth slightly longer than that of the container. The cover is fixedly attached to the mounting surface. The internal dimensions of the open base of the cover correspond closely to the external dimensions of the container holder so that the holder fits snugly into the cover. This allows enough space for vertical movement but not enough to permit tampering. The cover is made preferably of the same material used for the holder. In FIGS. 7 and 8 the container-holder is connected to the chassis by an open, two-armed, straight-sided frame that extends vertically down from the lower end of the vertical bar of the chassis, with one bar on each side of the upper part of the cover when the chassis is in its secured position. The frame is slightly wider and longer than the container cover to allow the holder to be lowered fully out of the cover before removing the unit, and to be clear of, and below, the cover when the unit is replaced. The open structure of the bracket allows for passage around the cover, which is fixed to the mounting surface. The vertical side elements of the open bracket are joined below, and the bracket extends down with a single arm that is fixed to the posterior surface of the container holder (i.e. toward the mounting surface and away from the subject). The lower end of the attaching bracket, preferably, fits closely into a notch-like space behind the lower back of the cover. A disposable, rubber-like sheath or other clean covering can be placed over the lower bracket and container-cover before each use. When the chassis is lowered for removal, the sheath is pulled off the container cover and encloses the container-holder to provide a clean surface.

Many embodiments can apply the essential feature of this one, i.e. a container held in the portable unit and its cover permanently attached to a mounting surface. Offsetting the cover from its attachment permits a single-armed bracket for the container-holder instead of the open-rectangle type. The chassis mount would use two brackets set at right angles with a lock in each. Alternatively a single-armed "C"-type bracket could replace the open rectangle and use a container-cover similar to that in FIGS. 11 and 12. The preferred embodiment is easier for most subjects to remove from, and secure to, the mount.

When the locking mechanism of the chassis is open (i.e. when the pistons are retracted) interruption of any element of either hand contact automatically closes the lock (i.e. extends the pistons) so that the unit cannot be fully replaced in its mount. The needle-like "key" extending from the closed end of each cylinder projects into its piston when the chassis is locked in the mounting bracket and maintains a switch within the piston in position to retract the piston when the restricting contacts are properly grasped. Piston retraction, therefore, does not occur if the pistons are not in the cylinders where the "key" sets the switch for retraction. Thus, if a hand engagement is broken and a piston is released to its projecting (i.e. locking) position during the time that the chassis is not in its mount, the piston does not retract if a subject reengages the contact. The unit, therefore, cannot be properly replaced and the breach of restriction is evident. The pistons can then be withdrawn only by using a key similar to the element in the cylinder housings of the bracket. As with the embodiment of FIGS. 3 through 6, other keys or programmed delays can be used to prevent a subject from retracting the pistons after the initial, prescribed engagement with the hand contacts.

The height of the unit from the open end of the container to the cross-bar preferably is made sufficient for convenience in using the containers and to prevent a subject from elevating the container to the level of the mouth. (Cylindrical hand-hold guards, fixed to the cross-bar, would prevent the wrist flexion needed for such attempts.) A foot attachment may be used to ensure separation of the legs when the hands are restricted so as to prevent a false specimen from being held between them. The foot restricting element consists preferably of a simple base plate with a foot switch at each end. The two switches are separated and require sufficient force so that a seated or a standing subject must keep both feet on the switches and apart so that the legs cannot hold a container. This element preferably is connected to the mounting bracket to retract a piston housed in the bracket, rather than the chassis, to simplify transmission. When a foot-restricting element is used, all four limbs must be restricted together to release the chassis.

The embodiment of FIGS. 7 through 12 can be modified to combine all the elements, including the container cover, into one portable unit. Securing locks for the unit are not necessary. The cover for such a unit is lifted clear when the restricting contacts are properly engaged. The supporting structure for the container-holder is then solid (instead of an open frame needed to pass over some wall-mounted covers.) The cover may be raised mechanically using the subject's hand movement, but battery power is preferred for this embodiment. The cover, open at the bottom, fits closely and is raised and lowered by a screw-drive and guide rail to expose and cover the container. Disengaging, or releasing the group of the hands at any time immediately locks the cover in its position and is evidence of a premature breach. Completely portable, self-contained embodiments are generally less secure and they are less convenient for voiding. Counters can be added to the various embodiments so as to record the number of times the device is employed.

Many other embodiments of this invention are feasible. They may be entirely portable entirely fixed or partly fixed and partly portable. Different means can be used to engage a subject, to secure and expose a container, to collect or divert a urine stream, to signal actions and to power the units. All embodiments have three essential features to carry out the method of this invention: (1) Means to require that at least one hand be engaged before the container is accessible. (2) Means to ensure the discovery of any premature disengagement (3) Means to make the container inaccessible after proper use.

I claim:

1. A method to prevent tampering with a procedure of collecting a specimen from a human subject comprising providing a hand hold for engaging each of the subject's hands, providing a specimen container, preventing access for voiding into said container until each of the hands is engaged, at least one hand of the subject being engaged by requiring said one hand to be located in a grasping position on the hand hold, affording access for voiding into said container for so long as each hand is engaged, and preventing further access to the container when said procedure is terminated.

2. A method according to claim 1 wherein said procedure is terminated if the subject removes said one hand away from said grasping position.

3. A method according to claim 1, including the step of enclosing said container in a container holder having a lockable closure, said step of affording access comprising the steps of unlocking the closure and displacing the closure to expose the container to receive the specimen, and said step of preventing further access comprising the steps of replacing the closure and locking the same in closed position.

4. A method according to claim 3 including the step of aborting the collecting procedure if the subject removes said one hand from its grasping position before the closure is replaced and locked.

5. A method according to claim 4 wherein said step of aborting the procedure is effected by locking the closure of the container holder in the open position.

6. A method according to claim 1 including the step of requiring the subject to grasp the hand holds first to afford access to said container and thereafter to prevent further access to the container.

7. A method according to claim 6 including the steps of providing contact actuators on the hand holds for activation by selected parts of the subject's hands to establish said grasping positions, and requiring the subject to activate the contact actuators of the hand holds to afford said access to the container and to prevent said further access to the container.

8. A method according to claim 1 including the step of positioning the container in a sufficiently small area accommodating the subject to assure that a true specimen is voided into the container by the subject, and that a false specimen not voided by the subject is not deposited into the container while said container is in said small area.

9. A method according to claim 1 including the step of providing contact actuators for each foot of the subject, and requiring engagement of the feet of the subject with said contact actuators from the time when access to the container is afforded until the time when further access to the container is prevented.

10. A method of collecting a specimen from a subject comprising the steps of:

providing a container into which the subject may void to create a specimen, enclosing the container in two-part container holder having a latch to interlock the two parts of the container holder, engaging the subject's hands so as to limit the freedom of the hands for other activity by the subject for a controlled period, unlocking the container holder and separating the parts to expose the container for acceptance of the specimen voided by the subject within said controlled period, maintaining said parts separated during said controlled period, reuniting the parts at the end of the period and locking the parts together, and providing latch means on the two parts actuatable to one position to be disengaged to unlock the parts for opening and to a second position to be engaged to relock the parts upon closure and operable in the event of actuation to the second position when separated to prevent relocking of the container holder parts, said engaging step including the step of providing a hand engaging device operable to actuate the latch means to the one position only upon placement of the subject's hand in a grasping position on said device and operable to actuate the latch means to the second position upon any displacement of said hand away from said grasping position.

11. A method according to claim 10 wherein said hand engaging device is provided with contact actuators to be activated by placement of selected parts of the subject's hands on said contact actuators, and requiring the subject to activate said contact actuators and grasp said hand engaging device to perform said step of unlocking the container holder and separating the parts.

12. A method according to claim 11 including the step of linking the contact actuators with the latch means so that deactivation of said contact actuators by removal of any one of said selected parts of the subject's hands from said contact actuators actuates the latch means to the second position either to relock the parts or to prevent locking of the container holder.

13. A method according to claim 10 wherein the container holder for the container is portable and is provided with two hand holds for engaging two hands of the subject, and including the step of providing a separate contact actuator on each hand hold and coupling said actuators to the latch means to actuate the latch means to the second position if either hand is displaced from its hand hold.

14. A method according to claim 13 including the step of requiring the subject to carry the container and container holder into a sufficiently small area accommodating the subject to assure that a true specimen is voided into the container by the subject, and that a false specimen not voided by the subject is not deposited into the container when in said small area.

15. A method according to claim 10 including the steps of providing foot-engaging elements and engaging the feet of the subject from the time before access to the container is afforded until the time when further access to the container is prevented.

16. A method according to claim 15 including the step of engaging feet of the subject with pressure-sensitive, electrical contact switches from the time before access to the container is afforded until the time when further access to the container is prevented, said switches being activated by presence of the subject's feet on the switches.

17. Apparatus to prevent tampering with or substitution of a specimen from a subject comprising:

a specimen container into which the subject may void to produce the specimen, a container holder for said specimen container with means to effect exposure and closure of said specimen container to afford and deny respectively access to said specimen container, said specimen-container holder enabling the subject to void directly into said specimen container when it is exposed, a pair of hand holds operatively connected to the container exposure and closure means of said container holder, each hand hold having contact actuators responsive to the placement of the subject's hands in grasping positions on said hand hold, and latch means on said container holder operable to be disengaged upon initial placement of the subject's hands in the grasping positions on said hand holds and operable to be engaged in the event one of the subject's hands is displaced from the grasping position on at least one hand hold, said latch means operable to lock the container holder if engaged while the container holder is closed and operable to prevent closure of the container if engaged when the container holder has allowed exposure of the specimen container, and means to prevent disengagement of said latch means after the engagement of said latch means.

18. Apparatus to prevent tampering with or substitution of a specimen from a subject comprising:

a container into which the subject may void to produce the specimen, a container holder for said container having two parts with intercooperating latch means and means to effect separation and closure of said two parts to afford and deny respectively access to said container, said container holder parts when separated enabling the subject to void directly into said container, a pair of hand holds operatively connected to said container holder and cooperable with said two parts to afford said separation and closure, each hand hold having hand contact devices responsive to the placement of the subject's hand in a grasping position on said hand hold, and latch means on said two-part container holder operable to be disengaged upon initial placement of the subject's hands in the grasping positions on said contact devices and operable to be engaged in the event one of the subject's hands is displaced from the grasping position on at least one contact device, the engagement of said latch means operable to lock the container holder when engaged while the two-part container holder is closed and operable to prevent closure of the container holder if engaged when the two-part container holder is separated, and means to prevent disengagement of said latch means after the engagement of said latch means.

19. Apparatus according to claim 18 wherein said two parts of the container holder comprise a receiver and a lid respectively, said receiver having an open top to accommodate said container, and said lid adapted to telescopically engage over said open top, said latch means comprising a piston on one of said parts, and keeper on the other of said parts, said piston operable to be extended and when the lid is engaged over the top to engaged in said keeper to latch the lid to said receiver and deny access to the container, and operable to be retracted and disengaged from the keeper to afford access to the container, said piston operable when the lid is not engaged over the top to be extended to prevent the telescopic engagement of said lid over the top.

20. Apparatus according to claim 18 wherein said two parts of the container holder comprise a receiver and a lid respectively, said receiver having an open top to accommodate said container, and said lid adapted to telescopically engage over said open top, said apparatus including means to limit the displacement of said lid to unidirectional separation above said open top, so that the subject must void into the container from one side of the open top between the top of the receiver and the lid, said lid being transparent.

21. Apparatus according to claim 18 wherein said two parts of the container holder comprise a receiver and a lid respectively, said receiver having an open top to accommodate said container, said apparatus including means to limit the separation of said lid to a limit position spaced from said open top so that the subject must void into the open top when the lid is in said limit position.

22. Apparatus according to claim 18 wherein said container holder is mounted in a compartment having means to confine the movement of the subject so that the subject when placing both hands in the engaged positions on the respective hand holds must assume a preset position in which the public and genital area of the subject is in a position relative to the container holder to afford voiding directly into the container, the means to confine the movement operable to prevent the subject from moving out of said present position and substituting a specimen which was not voided directly into said container.

23. Apparatus according to claim 22 wherein said means to confine movement includes a foot-engaging element including a pair of contact actuators spaced apart a distance which requires separation of the legs a distance to prevent the holding of a false-specimen supply device between the legs of the subject.

24. Apparatus to prevent tampering with or substitution of a specimen from a subject comprising a chassis having a stem, a container into which the subject may void to produce the specimen, a container holder for the container mounted on said stem and having two parts with container holder-control means to effect separation and closure of the two parts to afford and deny respectively access to the container, said container holder parts when separated enabling the subject to void directly into said container, a pair of hand holds mounted on said chassis and operatively connected to said means to effect separation of said two parts, each hand hold having hand contact actuators responsive to the placement of the subject's hand in an engaged position on its associated hand hold, and operable upon placement of the subject's hands in said engaged position to activate said container holder-control means, said container holder-control means operable upon activation to separate said two parts, then maintain the parts separated for a period to allow the subject to void directly into the container, and then effect closure of the two parts in a continuous sequence, said control means being inactivated upon any displacement of the subject's hand from the engaging positions, inactivation of said control means interrupting said sequence and preventing closure of said two parts.

25. Apparatus according to claim 24 wherein the hand engaging devices have contact actuators for activation by selected parts of the subject's hand, simultaneous engagement of all of said contact actuators being needed to activate said container holder control means.

26. Apparatus according to claim 25 wherein said contact actuators are positioned for activation by all of the fingers and the base of each hand of the subject.

27. Apparatus according to claim 24 wherein said chassis includes a cross bar transverse to said stem, said pair of hand holds being mounted on said cross bar.

* * * * *

UNITED STATES PATENT AND TRADEMARK OFFICE
CERTIFICATE OF CORRECTION

PATENT NO. : 5,223,221

DATED : June 29, 1993

INVENTOR(S) : Herbert W. Copelan

It is certified that error appears in the above-identified patent and that said Letters Patent is hereby corrected as shown below:

Column 1, line 36, "flase" should be --false--;

Column 2, line 48, delete "restricting";

Column 2, line 55, delete "restricting";

Column 4, line 46, after "shown in" insert -- Figs. 7 through 12--;

Column 5, line 8, after "engages" insert --each--;

Column 5, lines 14-15, delete "restricting";

Column 6, line 52, delete "restricting";

Column 6, line 53, "verticle" should be --vertical--;

Column 8, line 18, delete "restricting";

Column 8, line 43, delete "restricting";

UNITED STATES PATENT AND TRADEMARK OFFICE

CERTIFICATE OF CORRECTION

PATENT NO. : 5,223,221
DATED : June 29, 1993
INVENTOR(S) : Herbert W. Copelan

It is certified that error appears in the above-indentified patent and that said Letters Patent is hereby corrected as shown below:

Column 8, line 57, "is" should be --can be--.

Signed and Sealed this

Eleventh Day of January, 1994

Attest:

Bruce Lehman

BRUCE LEHMAN

Attesting Officer

Commissioner of Patents and Trademarks